United States Patent
Kataoka et al.

(10) Patent No.: US 6,668,038 B2
(45) Date of Patent: Dec. 23, 2003

(54) X-RAY FLUORESCENCE SPECTROMETER

(75) Inventors: Yoshiyuki Kataoka, Takatsuki (JP); Yasujiro Yamada, Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 183 days.

(21) Appl. No.: 10/006,584

(22) Filed: Dec. 10, 2001

(65) Prior Publication Data

US 2003/0118148 A1 Jun. 26, 2003

(51) Int. Cl.[7] .............................................. G01N 22/00
(52) U.S. Cl. ................................... 378/45; 378/44
(58) Field of Search .............................. 378/45, 44, 46, 378/50, 48, 42

(56) References Cited

U.S. PATENT DOCUMENTS

| | | | | |
|---|---|---|---|---|
| 4,959,848 A | * | 9/1990 | Parobek | 378/46 |
| 6,154,517 A | * | 11/2000 | Takahashi | 378/46 |
| 6,292,532 B1 | * | 9/2001 | Kawahara et al. | 378/49 |
| 6,370,220 B1 | * | 4/2002 | Stoop | 378/45 |
| 6,577,704 B1 | * | 6/2003 | Holz | 378/44 |

\* cited by examiner

*Primary Examiner*—David V. Bruce
*Assistant Examiner*—Irakli Kiknadze
(74) *Attorney, Agent, or Firm*—Sughrue Mion, PLLC (57) ABSTRACT

Where an object to be analyzed in an X-ray fluorescence analysis is a thin film sample, the X-ray fluorescence spectrometer facilitates selection of proper secondary X-ray lines to be measured to thereby facilitate an accurate analysis. The spectrometer includes a measuring line evaluating means 23 operable to calculate for each specified secondary X-ray line to be measured, a first theoretical intensity at a specified thickness and a composition of each of layers in the thin film and a second theoretical intensity at the thickness and the composition thereof when the thickness or a concentration has been changed by a predetermined quantity, to calculate a precision of a thickness or a precision of the concentration based on the first and second theoretical intensities, and to determine applicability or inapplicability of an analysis using the specified secondary X-ray line to be measured.

7 Claims, 6 Drawing Sheets

Measuring Line: Cu-K$\alpha$

Overall Intensity: 7250.19

| Layer # | (1) Layer Intensity | (2) Single Layer Intensity | (3) Attenuation Ratio | (4) Ratio to Infinite Thickness |
|---|---|---|---|---|
| 1 | 76.65 | 76.65 | 1.0000 | 0.0176 |
| Substrate | 7173.54 | 7300.69 | 0.9826 | 1.0000 |

X-RAY FLUORESCENCE SPECTROMETER

BACKGROUND OF THE INVENTION

1. Field of the Invention

The present invention relates to an X-ray fluorescence spectrometer for measuring the intensity of secondary X-rays emitted from a sample which has thin films such as, for example, a semiconductor wafer by irradiating the sample with primary X-rays.

2. Description of the Prior Art

Hitherto, a so-called X-ray fluorescence spectrometer has been well known and widely used for measuring the intensity of secondary X-rays such as fluorescent X-rays emitted from elements contained in a sample by irradiating the sample with primary X-rays and for subsequently determining the concentration of each of the elements or thickness of a film in the sample based on the measured intensity. In the practice of the X-ray fluorescence analysis performed with the use of such analyzing apparatus, depending on the type of the sample to be analyzed, appropriate analytical conditions, for example, the component (element) of interest for analysis, secondary X-ray lines to be measured, the atmosphere in which measurement is carried out, and, the number of orders of calibration curves vary. Accordingly, in the conventional X-ray fluorescence spectrometer, an operator of the analyzing apparatus has determined and set appropriate analytical conditions based on his or her experience.

However, with a so-called thin film sample such as, for example, it often occurs in semiconductor wafers, both the thickness and the composition of each of layers of the thin film are analyzed and that the same elements are contained in different layers. Accordingly, selection of the secondary X-ray lines to be measured is not easy for the operator and, once the selection is inappropriate, no accurate analysis is possible any longer.

SUMMARY OF THE INVENTION

In view of the foregoing, the present invention has been devised to substantially eliminate the above discussed inconveniences inherent in the conventional X-ray fluorescence spectrometer and is intended to provide an improved X-ray fluorescence spectrometer capable of performing an accurate analysis by facilitating selection of proper secondary X-ray lines to be measured where the sample to be analyzed is a thin film sample.

In order to accomplish the foregoing object of the present invention, in one aspect of the present invention, there is provided an X-ray fluorescence spectrometer for measuring intensities of secondary X-rays emitted from a sample, which includes a single layered thin film or a multi-layered thin film formed independently or on a substrate, by radiating the sample with primary X-rays, which apparatus includes a measuring line evaluating means and a display control means. The measuring line evaluating means is operable to calculate, for each specified secondary X-ray line to be measured, a first theoretical intensity at a specified thickness and a composition of each of layers of the thin film and a second theoretical intensity at the thickness and the composition thereof when the thickness or a concentration has been changed by a predetermined quantity, to calculate a precision of a thickness or a precision of the concentration based on the first and second theoretical intensities, and to determine applicability or inapplicability of an analysis using the specified secondary X-ray line to be measured based on the calculated thickness precision or the calculated concentration precision. The display control means is adapted to cause a display unit to display the applicability or inapplicability of the analysis determined by the measuring line evaluating means.

With the X-ray fluorescence spectrometer of the structure described above, since the applicability or inapplicability of the analysis of the thin film sample with the specified secondary X-ray line to be measured can be displayed, the operator can easily and properly select the proper secondary X-ray lines to be measured and, accordingly, an accurate analysis is possible.

In a preferred embodiment of the present invention, the measuring line evaluating means may determine whether or not the specified secondary X-ray line to be measured can be applied to a calibration curve method depending on a presence or absence of a specification for the analysis of the concentration in the layer where the specified secondary X-ray line to be measured is applied in an analysis of the thickness of the layer based on the calibration curve method, or depending on the presence or absence of the specification of the analysis of the thickness of a layer where the specified secondary X-ray line to be measured is applied to an analysis of the concentration of the layer. The display control means then causes the display unit to provide a visual indication of the applicability or inapplicability to the calibration curve method so determined by the measuring line evaluating means.

According to the above described embodiment, since the applicability or inapplicability of the specified secondary X-ray line to be measured to the calibration curve method is displayed, the operator can, based on the displayed indication, select a proper secondary X-ray lines to be measured easily particularly when the analysis is to be performed with the calibration curve method, so that an accurate analysis can be performed.

In another aspect of the present invention, there is provided an X-ray fluorescence spectrometer for measuring intensities of secondary X-rays emitted from a sample, which is a single layered thin film or a multi-layered thin film formed independently or on a substrate, by irradiating the sample with primary X-rays, which apparatus includes a measuring line evaluating means and a display control means. The measuring line evaluating means is operable to calculate, for each secondary X-ray emitted from the sample, a first theoretical intensity at a specified thickness and the composition of each of the layers of the thin film and a second theoretical intensity at the thickness and the composition thereof when the thickness or the concentration has been changed by a predetermined quantity, to calculate a precision of a thickness or a precision of the concentration based on the first and second theoretical intensities, and to select the secondary X-ray line to be measured based on the calculated thickness precision or the calculated concentration precision along with determination of applicability or inapplicability of the analysis using the secondary X-ray line to be measured so selected. The display control means is adapted to cause a display unit to display the applicability or inapplicability of the analysis determined by the measuring line evaluating means.

With the X-ray fluorescence spectrometer of the structure described above, since with respect to the thin film sample, the secondary X-ray lines to be measured can be automatically and properly selected by the measuring line evaluating means based on the calculated thickness precision or the calculated concentration precision, the operator need not to select the secondary X-ray lines to be measured which is one of the analytical conditions and an accurate analysis can be performed. Moreover, since the applicability or inapplicability of the analysis of the thin film sample with the automatically selected secondary X-ray lines to be measured can be displayed, the operator can easily perform an accurate analysis while avoiding an inaccurate analysis with reference to the display given by the display unit.

In a preferred embodiment of the present invention, the apparatus according to the second mentioned aspect of the present invention may further include a control device for executing an analysis of the sample according to predetermined analytical conditions and wherein the measuring line evaluating means applies the selected secondary X-ray lines to be measured to the control device as a portion of the proper analytical conditions depending on the applicability or inapplicability of the analysis so determined.

Where the control device is employed, the secondary X-ray lines to be measured that have been automatically selected can be automatically set as a part of the proper analytical conditions and, accordingly, the operator can be relieved from a burden of setting the secondary X-ray lines to be measured that form a part of the analytical conditions.

In the apparatus according to any one of the first and second mentioned aspects of the present invention, the measuring line evaluating means may preferably calculate, for each secondary X-ray line, theoretical intensities of a background thereof and then calculates a precision of a thickness or a precision of the concentration using the theoretical intensity of the background and the first and second theoretical intensities.

According to this embodiment, since the measuring line evaluating means calculates the thickness precision or the concentration precision using the theoretical intensity of the background together with the first and second theoretical intensities, determination of the applicability or inapplicability of the analysis with the secondary X-ray line to be measured can be performed more accurately and the operator can perform the accurate analysis based on that.

According to a further aspect of the present invention, there is provided an X-ray fluorescence spectrometer for measuring an intensity of secondary X-rays emitted from a sample, which is a single layered thin film or a multi-layered thin film formed independently or on a substrate, by irradiating the sample with primary X-rays, which apparatus includes a measuring line evaluating means and a display control means. The measuring line evaluating means is operable to calculate, for each specified secondary X-ray line, at a thickness value and a composition specified for each of the layers of the thin film, at least two numerical values from five numerical values including an overall intensity that is a theoretical intensity from the sample in its entirety; a layer intensity that is a theoretical intensity from the substrate or each layer of the thin film; a single layer intensity that is a theoretical intensity exclusive of an absorption of upper layers from the layer intensity; an attenuation ratio that is obtained by dividing the layer intensity by the single layer intensity; a ratio to infinite thickness that is a ratio of the single layer intensity at the specified thickness relative to the single layer intensity when the layer is deemed having an infinite thickness in terms of X-rays, and to select comments from pre-stored comments for the analysis based on the calculated numerical values. The display control means is adapted to cause a display unit to provide an indication of the numerical values and the comments both calculated and selected by the measuring line evaluating means.

With the analyzing apparatus according to the third mentioned aspect of the present invention, since the proper comments for the analysis together with the overall intensity, the layer intensity and others can be displayed by the display unit, the operator looking at the display unit can easily select the proper secondary X-ray lines to be measured and, therefore, can perform an accurate analysis.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENTS

Figure 1:
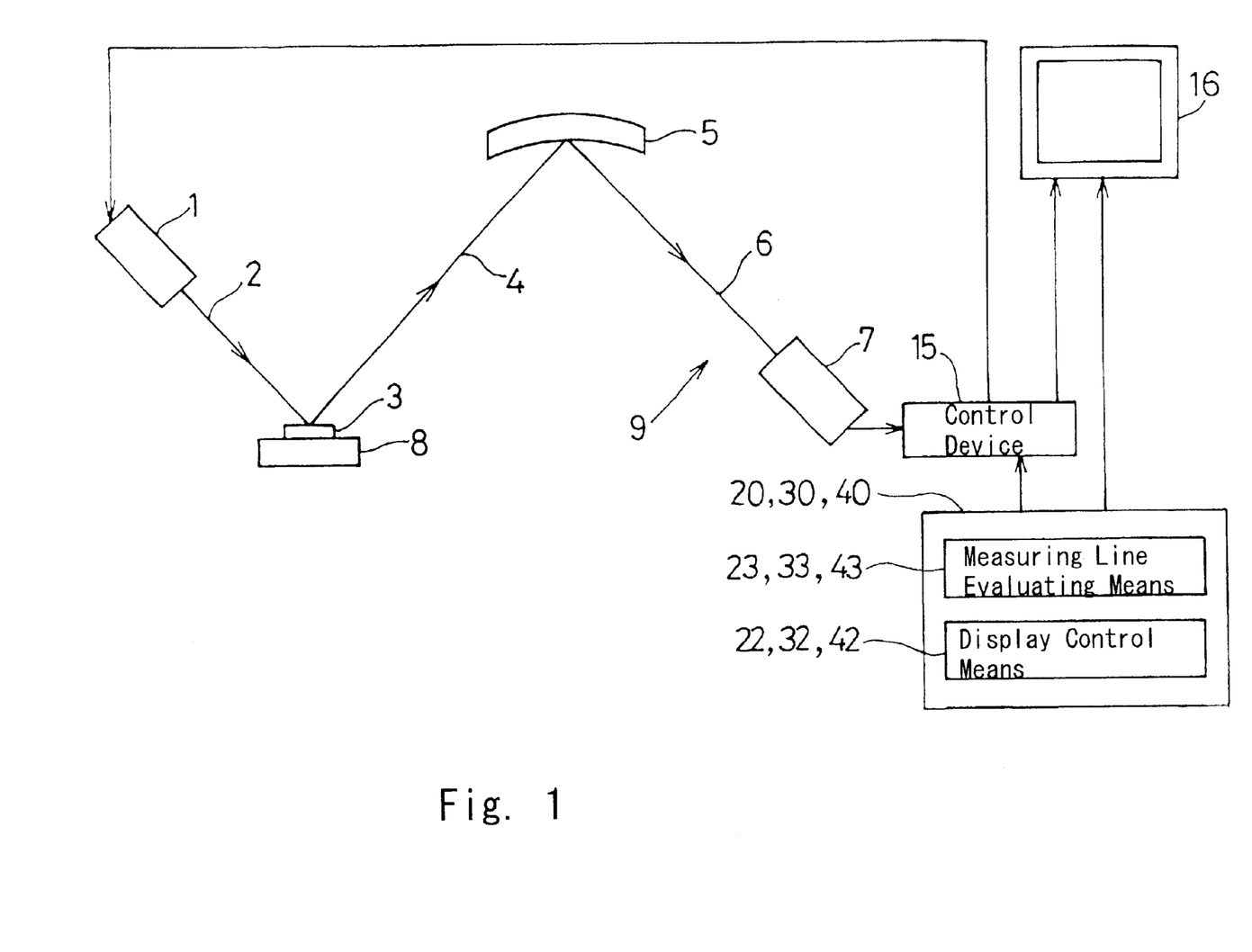
FIG. 1 is a schematic diagram showing an X-ray fluorescence spectrometer that can be used in the practice of any one of first to third preferred embodiments of the present invention.

With reference to FIG. 1, an X-ray fluorescence spectrometer according to the first preferred embodiment of the present invention will be described. As shown therein, the X-ray fluorescence spectrometer includes a sample support or table 8 for support thereon of a thin film sample 3 which may be either a single- or multi-layered includes an X-ray source 1 such as, for example, an X-ray tube for emitting primary X-rays 2 towards the sample 3, and a detecting means 9 for measuring the intensity of secondary X-rays 6 emitted from the sample 3 when the latter is generated by the primary X-rays 2. It is to be noted that where the sample 3 is the thin film formed on the substrate therein, the substrate shall be included in the sample 3. The detecting means 9 includes a spectroscopic device 5 for monochromating secondary X-rays 4 emitted from the sample 3 and a detector 7 for measuring the intensity of the secondary X-rays 6 for each wavelength that have been monochromated by the spectroscopic device 5.

The X-ray fluorescence spectrometer referred to above is a so-called scanning X-ray fluorescence spectrometer of a type in which the spectroscopic device 5 and the detector 7 are linked with each other by a goniometer. Hence, this X-ray fluorescence spectrometer furthermore includes a control device 15 for controlling the X-ray source 1, the goniometer, the detector 7 and other components to perform an analysis of the sample 3 under given analyzing conditions, a display unit 16 which may include a cathode ray tube or the like, and an analytical condition setting means 20 including a display control means 22 and a measuring line evaluating means 23 as will be described in detail subsequently.

The measuring line evaluating means 23 is operable to calculate, for each specified secondary X-ray line to be measured, a first theoretical intensity at a specified thickness and the composition of each of the layers of the thin film and a second theoretical intensity at the thickness and the composition thereof when the thickness or the concentration has been changed by a predetermined quantity, to calculate the precision of a thickness or the precision of the concentration based on the first and second theoretical intensities and finally to determine whether or not analysis by the specified secondary X-ray line to be measured is possible. It is to be noted that the measuring line evaluating means 23 can calculate, for each specified secondary X-ray line to be measured, the theoretical intensity of the background thereof and then calculate the precision of the thickness or the precision of the concentration based on the theoretical intensity of the background and the first and second theoretical intensities.

Also, the measuring line evaluating means 23 can determine whether or not the specified secondary X-ray line to be measured can be applied to a calibration curve method depending on a presence or absence of a specification of the analysis of the concentration in the layer of the thin film where the specified secondary X-ray line to be measured is applied to the analysis of the thickness of the thin film based on the calibration curve method, or depending on the presence or absence of the specification of the analysis of the thickness of a layer where the specified secondary X-ray line to be measured is applied to the analysis of the concentration of the layer.

The display control means 22 is operable to instruct the display unit 16 to provide a visual indication of possibility of the analysis so determined by the measuring line evaluating means 23 and whether or not application to the calibration curve method can be carried out.

Figure 2A:
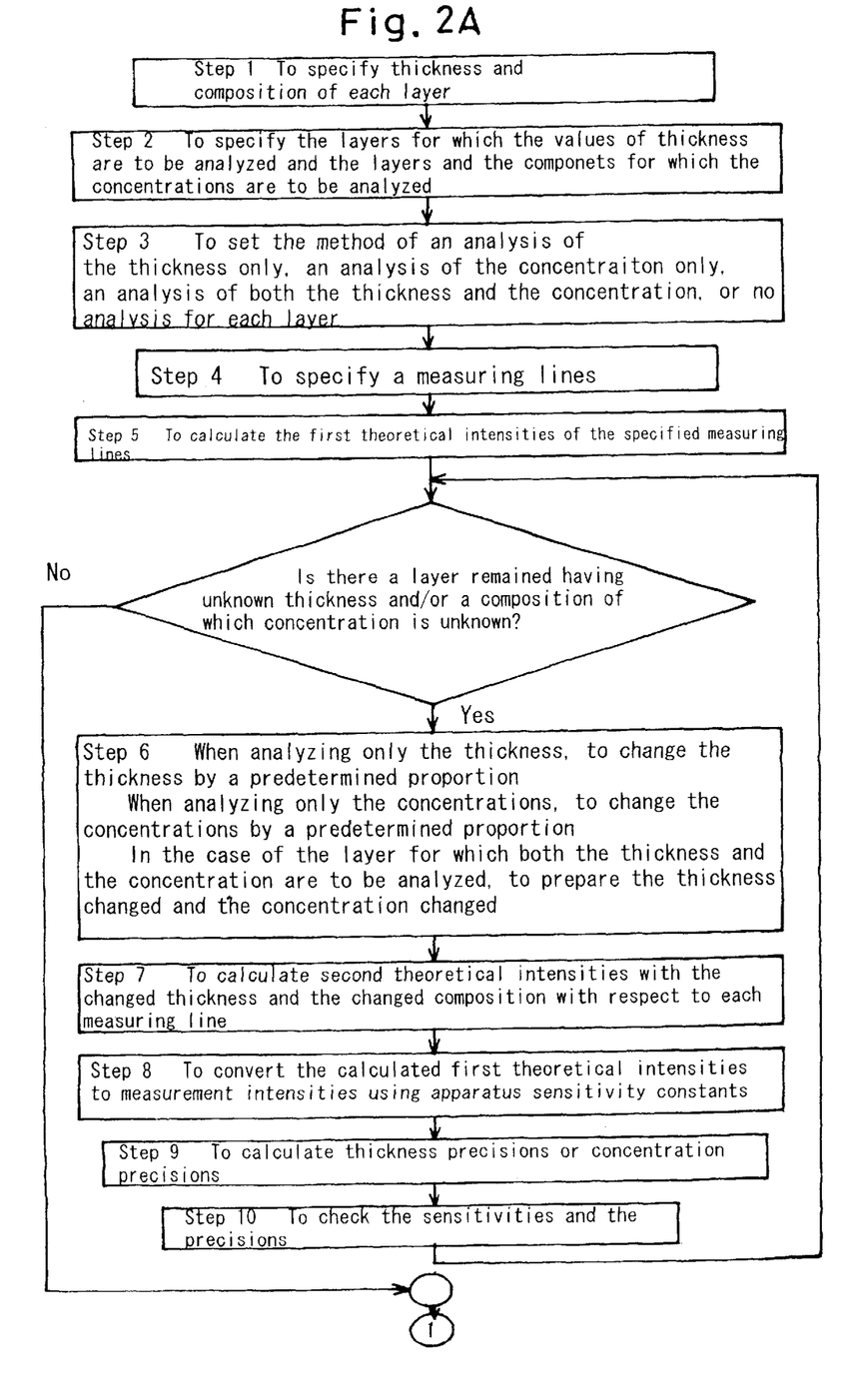
FIGS. 2A and 2B are flowcharts showing the sequence of operation of the X-ray fluorescence spectrometer according to the first embodiment of the present invention.
Figure 2B:
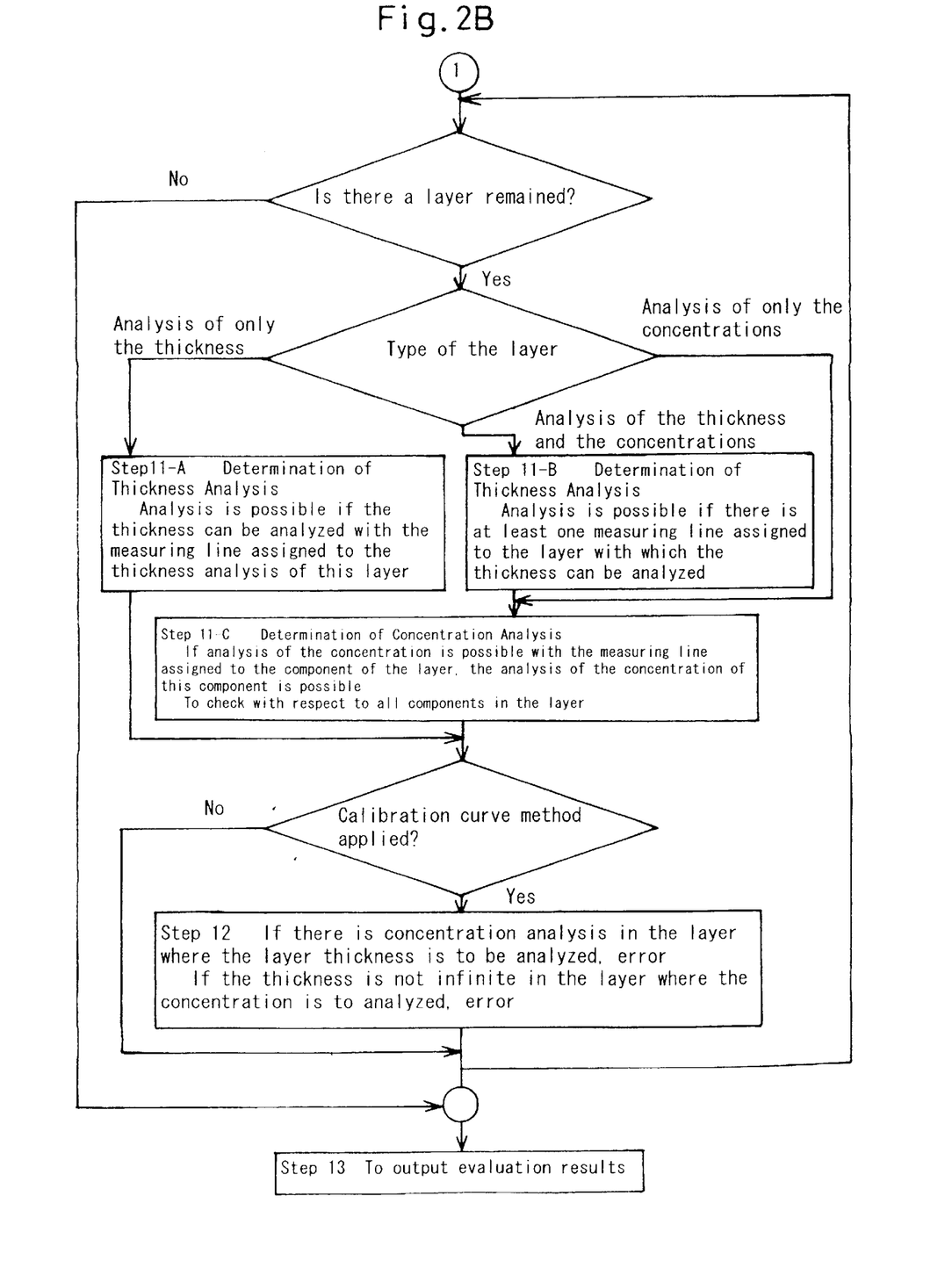

Hereinafter, the operation of the X-ray fluorescence spectrometer according to the first embodiment of the present invention will be described with reference to the flowchart of FIGS. 2A, 2B in connection with the analysis of the thickness and the composition of the thin film of the sample 3 of a copper substrate (a Cu layer) formed with a single layer thin film (a CuZn layer) consisting of copper and zinc. At the outset, using an input means (not shown) of the analytical condition setting means 20. (This input means is similarly used during specification and inputting performed by an operator, although not specifically referred thereto.), the operator specifies the thickness and the composition (set of concentrations) of each of the layers that may provide a basis for the calculation of the theoretical intensities. In this example, the operator specifies (Step 1), Cu 100 mass % with an infinity thickness (in terms of X-ray) for the Cu layer and Cu 60 mass % and Zn 40 mass % (balance) with a thickness of 100 nm for the CuZn layer. It is to be noted that the composition of the Cu layer (substrate) with the infinity thickness is known and, therefore, if it has been inputted beforehand, the operator need not input it at this stage.

Then, the operator specifies the layer of which thickness is to be analyzed and specifies the component of a layer of which concentration (concentration of a particular component) is to be analyzed. In this example, the operator specifies that the thickness of the CuZn layer is to be analyzed and the concentration of Cu in the CuZn layer is to be analyzed (at Step 2). Zn contained in the CuZn layer can be determined as the balance left by removing Cu.

Based on the contents specified at Steps 1 and 2, the measuring line evaluating means 23 (FIG. 1) sets, for each layer, one of the analysis of only the thickness, the analysis of only the concentration, the analysis of both the thickness and the concentration and none of those analysis. In this example, in a program, a flag indicating the analysis of both the thickness and the concentration is set for the CuZn layer and a flag indicating no analysis is set for the Cu layer (substrate) since both the thickness and the concentration of the Cu layer (substrate) have been known and need not be analyzed (Step 3).

Thereafter, the operator specifies the secondary X-ray lines to be measured (hereinafter also referred to as measuring lines) in a number equal to the number of unknown parameters. In this example, the unknown parameters are two, i.e., the thickness of the CuZn layer and the concentration of Cu and, therefore, Cu-Kα line is specified by assigning it to the thickness analysis and Zn-Kα is specified by assigning it to the concentration analysis (Step 4). In other words, in practice Cu is determined as the balance from Zn. As the measuring lines, characteristic X-ray lines from the X-ray tube or a background may be employed. In other words, they are also included in the secondary X-rays emitted from the sample and can be used for measuring lines. It is to be noted that at this stage it is possible to specify which one from the FP (Fundamental Parameter) method and the calibration curve method is to be used in performing the analysis.

The measuring line evaluating means 23 (FIG. 1) (unless otherwise specified, the main role of operation is performed by the measuring line evaluating means 23) then calculates, for each measuring line ip specified, a first theoretical intensity $I^T_O$ (ip) with the specified thickness and the composition by the FP method. In this example, the first theoretical intensities $I^T_O$ (ip) are calculated for Cu-Kα and Zn-Kα (Step 5).

Thereafter, the following steps 6 to 10 are sequentially performed for each of the layers. In the first place, with respect to the layers of which only thickness is to be analyzed, the specified thickness is changed by a predetermined quantity (including a predetermined rate. Hereinafter, the same.); with respect to the layer of which only concentration is to be analyzed, the concentration is changed by a predetermined quantity from the specified composition; and with respect to the layer of which thickness and concentration are both to be analyzed, the thickness and the specified composition are changed by a predetermined respective quantity from the specified thickness and the specified composition. In this example, in the CuZn layer of which thickness and concentration are to be analyzed, as shown by the following equations (1) and (2), the first set in which the thickness is changed by 1% (α=0.01) from the original thickness $T_{org}$ of 100 nm to $T_{new}$ of 101 nm while the composition is left unchanged, and the second set in which while the original thickness of $T_{org}$ is left unchanged the concentration of Cu is changed by a quantity ΔW=1 mass % from $W_{org}$ of 60 mass % to $W_{new}$ of 61 mass %, are prepared.

In the second set, the concentration of Zn that is the balance is 39 mass %. It is to be noted that in the case of the film having a plurality of layers of which concentrations are to be analyzed, the composition that is changed by a predetermined quantity for each of the layers are prepared (Step 6).

$$T_{new} = T_{org} \times (1.0 + \alpha) \quad (1)$$

$$W_{new}^i = W_{org} + \Delta W \quad (2)$$

Then, for each specified measuring line, using the thickness and the composition, which have been changed by the respective predetermined quantity, the second theoretical intensities $I^T_{diff}$ (ip) are calculated by the FP method. In this example, with respect to Cu-Kα and Zn-Kα, the second theoretical intensities $I^T_{diff}$ (ip) are calculated based on the above discussed first and second sets (Step 7).

Thereafter, using a apparatus sensitivity constant k (ip), the first theoretical intensities $I^T_O$ (ip) are converted into measurement intensity scale. In other words, since the theoretical intensities calculated by the FP method do not include apparatus factors (characteristics for each apparatus) unlike the intensities actually measured with the use of such apparatus, estimated measurement intensities $I^m_O$ (ip) (unit: kcps) are determined from the first theoretical intensities $I^T_O$ (ip) as shown by the following equation (3), using the apparatus sensitivity constant k (ip) that had been stored for each measuring line ip beforehand (Step 8).

$$I^m_O(ip) = k(ip) \times I^T_O(ip) \quad (3)$$

In the equation (3) above, the apparatus sensitivity constant k (ip) is determined as a ratio of the intensity, measured by such apparatus or an equivalent apparatus with the use of a representative standard material, to the theoretical intensity and is stored in the measuring line evaluating means 23 (FIG. 1). The measuring line not measured in such a way can be determined by interpolation or extrapolation from the measured apparatus sensitivity constants of the close lines in wavelength. It is to be noted that while the theoretical intensity is calculated using a distribution of the primary X-rays, a distribution of the primary X-rays is determined with characteristics for each type of X-ray tubes taken into consideration and is stored beforehand and, accordingly, the estimated measurement intensity can be determined with no problem even though the type of the X-ray tube to be used is changed.

Then, using the first and second theoretical intensities $I^T_O$ (ip) and $I^T_{diff}$ (ip) for each measuring line ip specified in the manner described above, the precision of the thickness or the precision of the concentration is calculated. Since in this example, both the thickness and the concentration in the CuZn layer are analyzed, the thickness precision and the concentration precision are calculated. In calculating these precisions, a relative precision SigInt of the estimated measurement intensity is calculated as shown by the following equation (4). It is to be noted that the measurement time t is assumed to be 40 seconds in this example.

$$SigInt = \{I^m_O(ip)/(t \times 1000)\}^{1/2} / I^m_O(ip) \quad (4)$$

Using this precision SigInt of the intensity, the relative precision SigThk of the thickness and the relative precision SigCnc of the concentration are calculated as shown by the following equations (5) and (6), respectively (Step 9).

$$SigThk = \alpha \cdot \frac{SigInt}{\frac{|I^T_o(ip) - I^T_{diff}(ip)|}{I^T_o(ip)}} \quad (5)$$

$$SigCnc = \frac{\Delta W}{W_{org}} \cdot \frac{SigInt}{\frac{|I^T_o(ip) - I^T_{diff}(ip)|}{I^T_o(ip)}} \quad (6)$$

Then, the sensitivity and the thickness precision in the case of the layer of which thickness only is to be analyzed, the sensitivity and the concentration precision in the case of the layer of which concentration only is to be analyzed, and, the sensitivity, the thickness precision and the concentration precision in the case of the layer of which both the thickness and the concentration are to be analyzed, are checked. In this example, with respect to the CuZn layer of which the thickness and the concentration are both analyzed, the sensitivity, the thickness precision and the concentration precision are checked in the following manner.

In the check of the sensitivity, if the estimated measurement intensity $I^m_O$ (ip) is smaller than a predetermined analyzable minimum intensity, for example, 0.001 kcps, the intensity is judged as insufficient sensitivity. This is true where the amount of deposit of the component thereof is extremely small or where even though the amount of deposit is large, most of the X-rays from the component are absorbed by upper layers With respect to the check of the thickness precision, if the relative precision SigThk of the thickness is not smaller than a predetermined check value, for example, 0.1, the analysis of the thickness is deemed impossible. This is true where the layer thereof has infinite thickness in terms of X-rays even when the relative precision SigInt of the previously described intensity is sufficiently acceptable (small).

With respect to the check of the concentration, if the relative precision SigCnc of the concentration is not smaller than a predetermined check value, for example, 0.1, the analysis of the concentration is deemed impossible. In this example, Cu-Kα is deemed unacceptable in both the thickness analysis and the concentration analysis. Results of the checks of the sensitivity, the thickness precision and the concentration precision of each of the measuring line are stored in the measuring line evaluating means 23 (FIG. 1) (Step 10).

Then, by performing the following steps 11 to 12 for each layer with the use of the result of the checks, determination of the possibility for the analysis by the specified measuring lines on the basis of the thickness precision or the concentration precision. In the case of the layer of which only the thickness is to be analyzed, if the result of the check with the use of the measuring line assigned to such layer indicates insufficient sensitivity, an error of such meaning is set. If the result of the check with the use of the assigned measuring line indicates that the analysis of the thickness is possible, it means that the analysis can be performed. However if it indicates that the analysis is impossible, an error to such meaning is set (Step 11-A). In the case of the layer of which only the concentration is to be analyzed, if the result of the check with the use of the assigned measuring line to a component of the layer indicates insufficient sensitivity, an error to such meaning is set. If the result of the check with the use of the measuring line assigned to a component of the layer indicates that the analysis of the concentration is possible, it means that the analysis of the component is possible, but if it indicates that the analysis of the concentration is impossible, an error to such meaning is set (Step 11-C).

In the case of the layer of which both the thickness and the concentration are to be analyzed, if the result of the check with the use of the measuring line assigned to the layer indicates insufficient sensitivity, an error to such meaning is set. If the result of the check with the use of the measuring line assigned to the layer indicates that there is even one measuring line with which the thickness can be analyzed, the analysis of the thickness is possible, but if there is no measuring line with which the thickness can be analyzed, an error to such meaning is set (Step 11-B) and then the program flow goes onto the step 11-C. At this step, if there is the measuring line with which neither the analysis of the thickness nor the analysis of the concentration is possible, an error to such meanings is set. In this example, an error to such meaning that in the CuZn layer neither the analysis of the thickness nor the analysis of the concentration with Cu-Kα is possible is set (Step 11-C).

In the next place, where there is a specification of the calibration curve method, if the specified measuring line is applied to the analysis of the thickness of the layer based on the calibration curve method, applicability or inapplicability to the calibration curve method is determined depending on the presence or absence of the specification of the analysis of the concentration of to the layer. It is because when the thickness of the layer is to be analyzed based on the calibration curve method, it is affected by the composition of the layer, the composition of the layer should be fixed. Thus, if there is a specification of the analysis of the concentration to the layer, a warning error indicating that with the calibration curve method the analysis of the thickness is impossible is set.

Also, where the specified measuring line is applied to the analysis of the concentration of the layer based on the calibration curve method, applicability or inapplicability to the calibration curve method is determined depending on the presence or absence of the specification of the analysis of the thickness to the layer or capability or incapability of the analysis of the thickness. It is because when the concentration of the layer is to be analyzed based on the calibration curve method, it is necessary for the thickness of the layer to be constant or to be of an infinite value in terms of the X-rays for the measuring line. Therefore, if there is the specification of the analysis of the thickness to the layer or the analysis of the thickness with the specified measuring line is possible, a warning error to such meaning that the calibration curve method cannot be applied to the analysis of the concentration is set (Step 12).

Thereafter, the display control means 22 (FIG. 1) causes the display unit 16 to provide an indication of an applicability or inapplicability of the analysis and applicability or inapplicability to the determined calibration curve method (Step 13) determined by the measuring line evaluating means 23 (FIG. 1) in the manner described above.

As described above, with the apparatus according to the first embodiment of the present invention, since the applicability or inapplicability of the analysis of the sample of the thin film with the specified measuring line can be displayed, the operator can, based on the displayed indication, select a proper measuring line so that an accurate analysis can be performed. Also, since the applicability or inapplicability of the specified measuring line to the calibration curve method is also displayed, the operator can, based on the displayed indication, select a proper measuring line easily particularly when the analysis is to be performed with the calibration curve method, so that an accurate analysis can be performed.

In the meantime, while there is no problem if the background intensity is extremely low as compared with the peak, it is necessary for the background intensity to be taken into consideration when a measuring line of a short wavelength is to be measured. It may occur that although the K line with a short wavelength will result in a higher intensity and a higher background as compared with the L line, but the precision of analysis would be better with the L line of a low background even though the intensity is smaller. Accordingly, in the apparatus according to the first embodiment, the measuring line evaluating means 23 (FIG. 1) can be used to calculate the theoretical intensity of the background for each specified measuring line and to calculate the thickness precision or the concentration precision using the theoretical intensity of the background thereof and the first and second theoretical intensities. In such case, at Step 8, the theoretical intensity of the background is calculated as the sum of the Compton scattering and the Thomson scattering, and is then converted to a measured intensity scale as shown by the following equations (7) and (8).

$$I_{TB} = I_{OB}(\lambda) \times I_{TBO}(\lambda) \tag{7}$$

$$I_{MB} = k(\lambda) \times I_{TB} \tag{8}$$

In these equations (7) and (8), ITBO ($\lambda$) represents the theoretical intensity of the background when the intensity of the primary X-rays is assumed to be 1.0, $I_{OB}$ ($\lambda$) represents a distribution of the primary X-rays, $I_{TB}$ represents the theoretical intensity of the background including of the intensity of the primary X-rays, k ($\lambda$) represents a background sensitivity coefficient of the wavelength $\lambda$, and $I_{MB}$ represents an estimated measured intensity of the background.

The background sensitivity coefficient k ($\lambda$) can be determined beforehand by measuring a sample with the use of the apparatus or its equivalent apparatus to thereby measure the background intensity for each wavelength and also by calculating the theoretical intensity, using an X-ray tube used in the measurement and the primary X-ray distribution of a tube voltage and is stored in the measuring line evaluating means 23 (FIG. 1). With respect to the background sensitivity coefficient k ($\lambda$) of the wavelength for which no background intensity has been measured, it can be determined by interpolation or extrapolation. While the theoretical intensity is calculated using the distribution of the primary X-rays, the distribution of the X-rays is determined in consideration of the characteristics for each type of the X-ray tubes and is stored beforehand, and therefore, even though the type of the X-ray tube to be used is changed, the estimated measured intensity can be determined with no problem.

It is to be noted that where the substrate is a single crystal such as a silicon wafer, the manner in which scattered X-rays are generated is in a specific condition and, moreover, the background tends to increase because of diffracted X-rays. In such case, the background sensitivity coefficient k ($\lambda$) is determined using the single crystal substrate used or the intensity ratio relative to any other amorphous or polycrystal sample is determined for each wavelength.

Then, at Step 9, in calculating the thickness precision and the concentration precision, the relative precision SigInt of the estimated measured intensity is calculated using the following equation (9) in place of the previously discussed equation (4).

$$SigInt = \{(i^m{}_O(ip) + I_{MB})/(t \times 1000)\}^{1/2}/I^m{}_O(ip) \tag{9}$$

Using the relative precision SigInt of the intensity taken into consideration together with the intensity of this background, subsequent calculations of the relative precision SigThk of the thickness and the relative precision SigCnc of the concentration are carried out in a manner similar to those described hereinabove. With the apparatus according to the first embodiment, since using the theoretical intensity of the background as well the thickness precision or the concentration precision can be calculated in the measuring line evaluating means 23 (FIG. 1), the applicability or inapplicability of the analysis based on the measuring line can be more accurately determined and the operator can perform a more accurate analysis based on it.

Hereinafter, the apparatus according to a second embodiment of the present invention will be described. In the first place, the structure of this apparatus will be described with reference to FIG. 1. This apparatus is for automatically selecting a proper measuring line and differs from the apparatus according to the previously described first embodiment in that the measuring line evaluating means 33 used in the apparatus of the second embodiment is so designed as to calculate, for each secondary X-ray line emitted from the sample, a first theoretical intensity at a specified thickness and the composition of each of the layers of the thin film and a second theoretical intensity at the thickness and the composition thereof when the thickness or the concentration has been changed by a predetermined quantity, to calculate the precision of a thickness or the precision of the concentration based on the first and second theoretical intensities, to select the secondary X-ray line to be measured based on the calculated thickness precision or the calculated concentration precision along with determination of applicability or inapplicability of the analysis using the secondary X-ray line to be measured so selected, and finally to apply the secondary X-ray line to be measured so selected to a control device as a portion of appropriate analytic conditions in accordance with the applicability or inapplicability of the analysis so determined.

Also, the measuring line evaluating means 33 employed in the apparatus of the second embodiment differs from the measuring line evaluating means 23 used in the apparatus of the first embodiment in that the measuring line evaluating means 33 employed in the apparatus of the second embodiment does not determine applicability or inapplicability of the measuring line to the calibration curve method. The other procedure thereof is similar to those in the apparatus of the first embodiment and, accordingly, the details are not reiterated while same parts are designated by the same reference numbers.

Figure 3A:
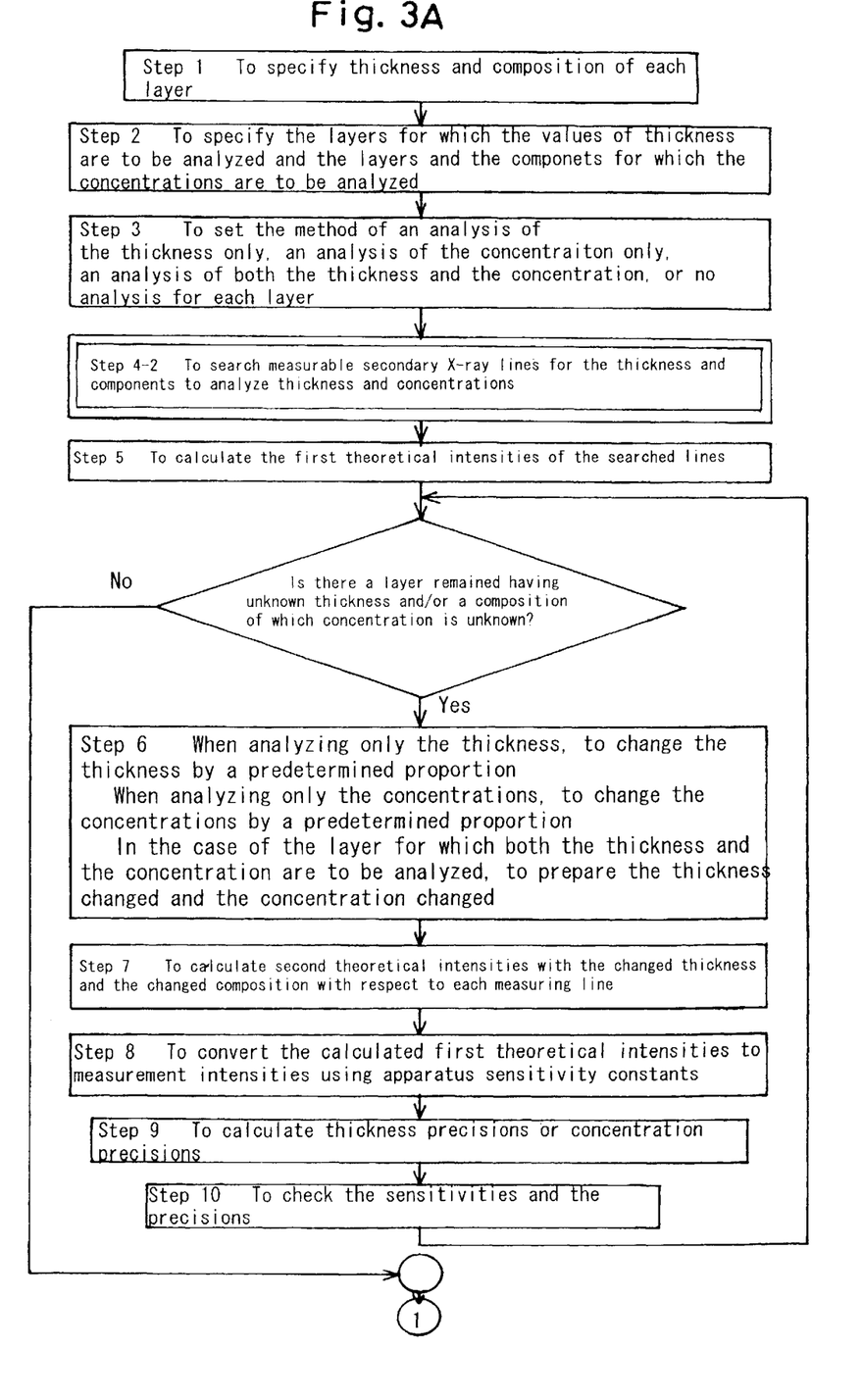
FIGS. 3A and 3B are flowcharts showing the sequence of operation of the X-ray fluorescence spectrometer according to the second embodiment of the present invention.
Figure 3B:
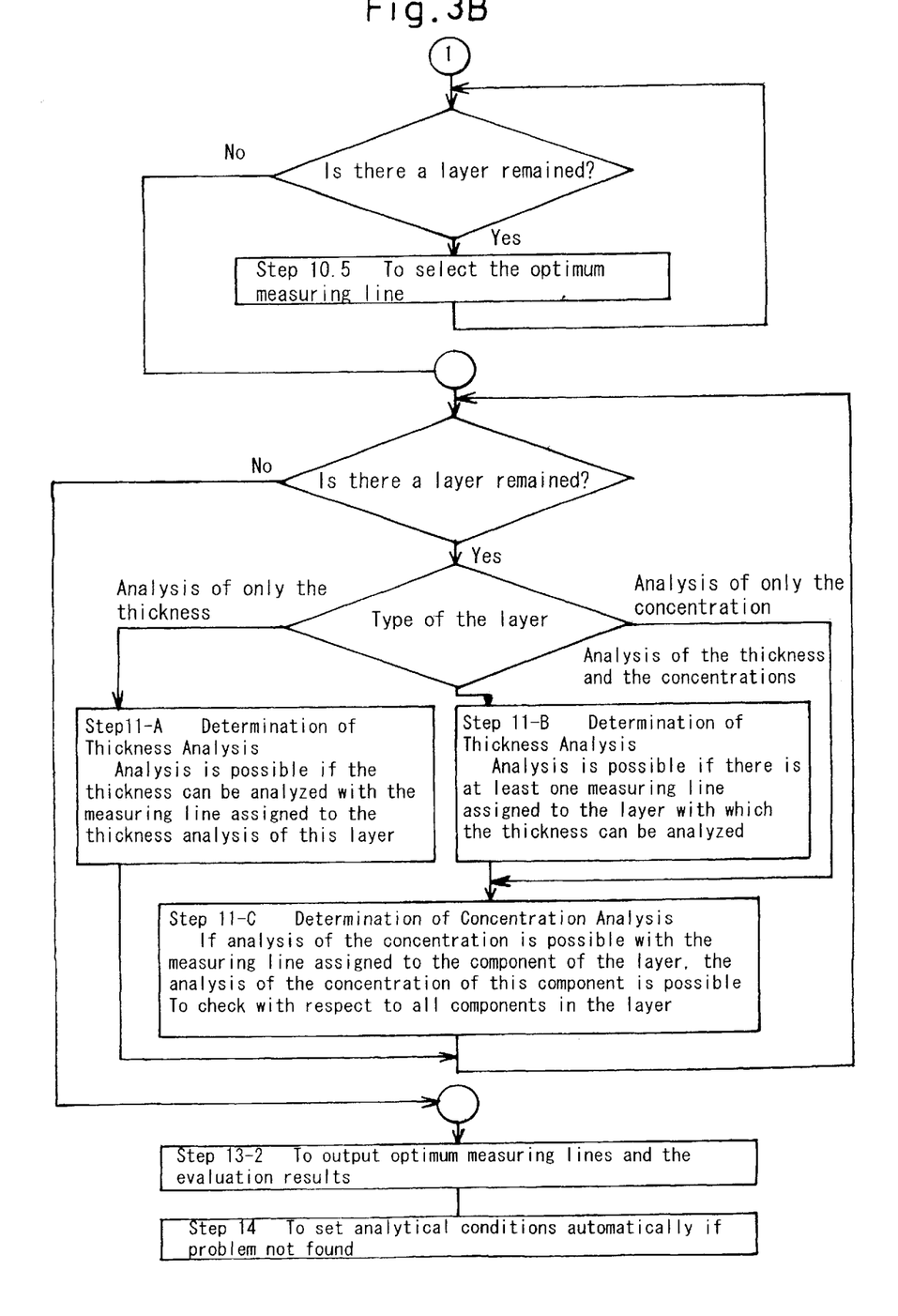

With particular reference to the flowchart shown in FIGS. 3A, 3B, the operation of the apparatus according to the second embodiment of the present invention will now be described as applied to the analysis of the thickness and the composition of the thin film of the sample 3 which, as is the case with that used in the apparatus according to the previously described first embodiment, is a copper substrate (the Cu layer) formed with a single layered thin film consisting of copper and zinc (the CuZn layer). It is to be noted that the process from Step 1 to Step 3 is identical with that described in connection with the first embodiment.

Subsequent to Step 3, based on the contents set at Step 3, the measuring line evaluating means 33 (FIG. 1) searches for measurable secondary X-ray lines (secondary X-ray lines that are candidates for selection of measuring lines) with respect to the component for which the thickness or the concentration is to be determined. In the case of the layer for which only the concentration is to be analyzed, for each component to be analyzed, elements to be measured, they are stored beforehand, are read out (for example, Al and Cu are used for in the case of $Al_2O_3$ and Cu, respectively) and all kinds of X-ray lines that can be measured for each element are read out. In the case of the layer for which only the thickness is to be analyzed, that is, in the case of the layer including the only one component or a plurality of components having a fixed composition, elements of the layer or elements of the components which are in the lower layer and the concentrations are fixed are called out and all kinds of X-ray lines that can be measured with each of those elements are called out.

In the case of the layer for which both the thickness and the concentration are to be analyzed, by assigning the thickness to the balance (residual) component and by reading out the elements to be measured with respect to each of components of which the concentrations are to be analyzed, all kinds of X-ray lines that can be measured for each element are called out. It is to be noted that instead of reading out all kinds of X-ray lines that can be measured for each element, they may be read out from $K\alpha$, $L\alpha$ and $M\alpha$ that are major X-ray lines. In this example, Cu-$K\alpha$, Cu-$L\alpha$, Zn-$K\alpha$ and Zn-$L\alpha$ are searched for (Step 4-2). Also, as is the case with the layer for which only the thickness is to be analyzed, elements to be measured and having a composition of which the concentration in the lower layers are fixed are called out and all kinds of X-ray lines that can be measured for each of those elements are called out.

Thereafter, with respect to the measuring line so searched for, as is the case with the apparatus according to the previously described first embodiment, a process from Step 5 to Step 10 is executed. As a result thereof, in this example, Cu-$K\alpha$ becomes impossible for the analysis of both of the thickness and the concentration.

Then, based on the calculated thickness precision or the calculated concentration precision, the optimum measuring line are selected. In the order from the top layer, they are selected in the following manner. As for the layer for which only the concentration is to be analyzed, the X-ray line of the best concentration precision (smallest) is selected from the X-ray lines assigned to the analysis for each component. On the other hand, as for the layer for which only the thickness is to be analyzed, the X-ray line of the best thickness precision (smallest) is selected from the X-ray lines assigned to the analysis.

In the case of the layer for which both the thickness and the concentration are to be analyzed, if there is the best (small) X-ray line for both of the concentration precision and the thickness precision for each element to be measured, such X-ray line is selected. If there is no such an X-ray line and the best X-ray line for the concentration precision is impossible to analyze the thickness, the X-ray line of the best thickness precision is selected. In the other cases, the X-ray line of the best concentration precision is selected. By this stage, the X-ray line for the thickness is assumed to be tentatively determined.

In the case of thin film analysis, a plurality of X-ray lines can be selected for the measuring lines for the same element. Accordingly, with respect to one of the X-ray lines selected in the manner described above, which exhibits the worst thickness precision, if there is an X-ray line that is one of the X-ray lines not selected, but exhibits a better thickness precision, selection is made by replacing it with the X-ray line exhibiting the worst thickness precision. Also, if of the X-ray lines of the elements contained in the lower layers there is an X-ray line exhibiting a better thickness precision, selection is made by replacing it with the X-ray line exhibiting the worst thickness precision. Where the selected X-ray lines overlap, one of them is changed to the next candidate X-ray line. In this example, Cu-$L\alpha$ and Zn-$K\alpha$ are selected by tentative determination, but Zn-$L\alpha$ is selected by the replacement of Cu-$L\alpha$ and finally Zn-$K\alpha$ and Zn-$L\alpha$ are selected (Step 10.5).

Thereafter, with respect to the measuring lines so selected, Step 11 is executed in a manner similar to that with the apparatus according to the first embodiment. As a result, in this example, the analysis is considered having no problem as to the thickness and the concentration using Zn-$K\alpha$ and Zn-$L\alpha$. It is to be noted that with the apparatus according to the second embodiment, since applicability or inapplicability of the measuring lines to the calibration curve method is not determined, Step 12 (FIG. 2B) is not executed. And, as is the case with the apparatus according to the first embodiment, the display control means 32 (FIG. 1) causes the display unit 16 to provide an indication of applicability or inapplicability of the analysis determined by the measuring line evaluating means 33 (FIG. 1) (Step 13-2).

As hereinabove described, with the apparatus according to the second embodiment of the present invention, since the measuring line for the thin film sample can be automatically and properly selected by the measuring line evaluating means 33 (FIG. 1) based on the calculated thickness precision or the calculated concentration precision, the operator need not select the measuring line for the analytical conditions and accurate analysis is therefore possible. Moreover, since the applicability or inapplicability of the analysis of the thin film sample with the automatically selected secondary X-ray lines to be measured can be displayed, the operator can easily perform an accurate analysis while avoiding an inaccurate analysis with reference to the display given by the display unit.

It is to be noted that even with the apparatus according to the second embodiment, the thickness precision or the concentration can be calculated using the theoretical intensity of the background too, as is the case with the apparatus according to the first embodiment.

Also, with the apparatus according to the second embodiment, the measuring line evaluating means 33 (FIG. 1) applies the selected measuring lines to the control device 15 (FIG. 1) as a portion of the proper analytical conditions based on the applicability or inapplicability of the analysis so determined. In this example, Zn-K$\alpha$ and Zn-L$\alpha$ are automatically set as the measuring line. Thus, with the apparatus according to the second embodiment, the operator can be relieved from a burden of setting the measuring line that is one of the analytical conditions.

The apparatus according to the third embodiment of the present invention will now be described. The apparatus used in the third embodiment of the present invention has a structure which will be described with reference to FIG. 1. As is the case with the apparatus according to any one of the previously described first and second embodiments, the apparatus includes the sample support 8, the X-ray source 1, the detecting means 9, the control means 15 and the display unit 16. This apparatus also includes an analytical condition setting means 40 made up of a display control means 42 and a measuring line evaluating means 43, which will be described in detail subsequently.

The measuring line evaluating means 43 is operable to calculate five numerical values as will be mentioned later and also to select comments from pre-stored comments for the analysis based on the calculated numerical values. The display control means 42 causes the display unit 16 to provide an indication of the numerical values and the comments both calculated and selected by the measuring line evaluating means 43. The numerical values referred to above, which are calculated for each specified secondary X-ray line, with a thickness and a composition specified for each of the layers of the thin film, include an overall intensity which is the theoretical intensity from the sample in its entirety; a layer intensity that is a theoretical intensity from each layer and the substrate in the thin film; a single layer intensity that is a theoretical intensity exclusive of absorption by the upper layers from the layer intensity; an attenuation ratio that is obtained by dividing the layer intensity by the single layer intensity; a ratio to infinite thickness that is a ratio of the single layer intensity at the specified thickness relative to the single layer intensity when the layer is deemed having infinite thickness in terms of X-rays.

The operation of the apparatus according to the third embodiment will now be described. In the case of the thin film sample in which the same element is contained in different layers, it often occurs that the analysis of neither the thickness nor the concentration of a particular layer can be performed efficiently and, therefore, the analysis has hitherto been performed by fixing the composition or the thickness of the particular layer. At this time, while evaluation of the measuring lines is carried out by calculating the theoretical intensities of the secondary X-ray lines emitted from the thin film sample, evaluation was not easy with the conventional apparatus since the theoretical intensities calculated and displayed represented the overall intensities that are the theoretical intensities from the thin film sample in its entirety. Therefore, in the apparatus according to the third embodiment of the present invention, the measuring line evaluating means 43 and the display control means 42 are employed to calculate the five numerical values, not only the overall intensity, but also such as the layer intensity, the single layer intensity, the attenuation ratio and the ratio to the infinite thickness, and also to select the comments from the pre-stored comments for the analysis based on the calculated numerical values, so that the calculated numerical values and the selected comments for the analysis can be displayed by the display unit 16.

As is the case with the apparatus according to any one of the first and second embodiments, reference will now be made to the analysis of the thickness and the composition of the thin film that is a single layer thin film made of copper and zinc (the CuZn layer) on the copper substrate (the Cu layer) of the sample 3. At the outset, the operator specifies the thickness and the composition (the concentrations of the layer) of each layer that provides a basis for the calculation of the theoretical intensities. In this example, the operator specifies Cu 100 mass % with infinity thickness (in terms of X-ray) for the Cu layer and Cu 60 mass % and Zn 40 mass % (balance) with a thickness of 100 nm for the CuZn layer. It is to be noted that the composition of the Cu layer (substrate) with infinity thickness is known and, therefore, if it has been inputted beforehand, the operator need not input it at this stage.

Figure 4:
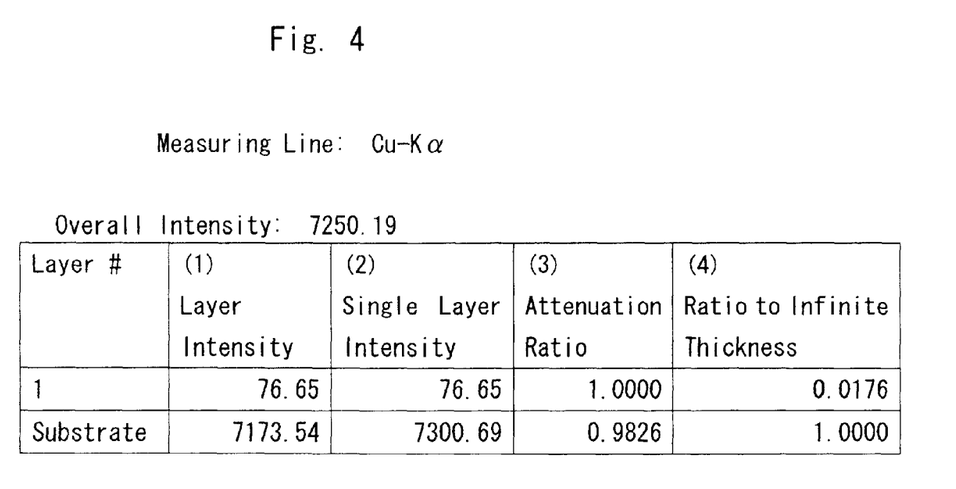
FIG. 4 is a diagram showing an example of a display given by the X-ray fluorescence spectrometer according to the third embodiment of the present invention.

Then, when the operator specifies Cu-K$\alpha$, from the measurable secondary X-ray lines, that is to be evaluated, such a display is shown in FIG. 4. The layer #1 stands for the CuZn layer. It can readily be understood that from the overall intensity and the layer intensity (1), most of Cu-K$\alpha$ X-rays are generated from the substrate. While the attenuation ratio (3) represents the degree of absorption by the upper layer, it can readily be understood that the absorption by the Cu—Zn layer of the Cu-K$\alpha$ generated from the substrate is very small.

The ratio (4) to the infinite thickness is a value obtained by dividing the single layer intensity (2) by the intensity that is calculated with the composition left unchanged and the thickness changed to an infinite value in terms of X-rays. It will readily be known that if the ratio (4) to the infinite thickness is equal to 1.0000 or a value close to it, the analysis of the thickness is not possible (as a matter of course, the substrate generally need not be analyzed). Conversely, if this value is small and not greater than 0.05, it means that the layer thereof is extremely thin in terms of X-rays and, therefore, only when the thin film is made of single layer and such layer is the top layer with the lower layer containing no same element, it will readily be known that the amount of deposit and the intensities has a linear relationship with each other.

With respect to the comments for the analysis, they are selected and displayed, for example, in a manner which will now be described. If the same elements are contained in the plural layers and, in the layer #n, the ratio of the layer intensity to the overall intensity is not greater than a predetermined value, for example, 0.05, a comment indicative of "The measurement is not possible as the intensity from the layer #n is too small compared with the overall intensity." is selected and displayed. On the other hand, if the attenuation ratio is not greater than a predetermined value, for example, 0.01 in the layer #n, a comment descriptive of "Measurable intensity is too small from the layer #n because the absorption by the upper layer is too large." is selected and displayed. If in the layer #n the ratio to the infinite thickness is not smaller than a predetermined value, for example, 0.95, a comment descriptive of "Measurement of the thickness of the layer #n is difficult since the intensity of the layer #n is close to infinite thickness." is selected and displayed.

As hereinabove described, with the apparatus according to the third embodiment of the present invention, since the proper comment for the analysis are displayed together with the overall intensity, the layer intensity and others, the operator can easily select the proper measuring lines based on that and can therefore perform an accurate analysis. It is to be noted that when the measuring line evaluating means 43 (FIG. 1) performs calculation of the overall intensity, the layer intensity, the single layer intensity, the attenuation ratio and the ratio to infinite thickness, it is possible to convert the theoretical intensity to a measurement intensity scale as is the case with Step 8 for the operation of the apparatus according to any one of the first and second embodiments. Also, by specifying not only the fluorescent X-rays, but also the background, the theoretical intensity of the background can be calculated and displayed using the previously discussed equations (7) and (8).

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. An X-ray fluorescence spectrometer for measuring intensities of secondary X-rays emitted from a sample, which includes a single layered thin film or a multi-layered thin film formed independently or on a substrate, by irradiating the sample with primary X-rays, said apparatus comprising:

a measuring line evaluating means for calculating, for each specified secondary X-ray line to be measured, a first theoretical intensity at a specified thickness and a composition of each of layers of the thin film and a second theoretical intensity at the thickness and the composition thereof when the thickness or the concentration has been changed by a predetermined quantity, for calculating a precision of a thickness or a precision of the concentration based on the first and second theoretical intensities, and for determining applicability or inapplicability of an analysis using the specified secondary X-ray line to be measured based on the calculated thickness precision or the calculated concentration precision; and a display control means for causing a display unit to display the applicability or inapplicability of the analysis determined by the measuring line evaluating means.

2. The X-ray fluorescence spectrometer as claimed in claim 1, wherein the measuring line evaluating means determines whether or not the specified secondary X-ray line to be measured can be applied to a calibration curve method depending on a presence or absence of a specification of the analysis of the concentration in the layers of the thin film where the specified secondary X-ray line to be measured is applied in the analysis of the thickness of a layer in the thin film based on the calibration curve method, or depending on the presence or absence of the specification of the analysis of the thickness of the layer in the thin film or applicability or inapplicability of an analysis of the thickness where the specified secondary X-ray line to be measured is applied to an analysis of the concentration of the layer in the thin film, and wherein the display control means causes the display unit to display applicability or inapplicability to a calibration curve method determined by the measuring line evaluating means.

3. The X-ray fluorescence spectrometer as claimed in claim 1, wherein the measuring line evaluating means calculates, for each secondary X-ray line, a theoretical intensity of a background thereof and then calculates a precision of a thickness or a precision of the concentration using the theoretical intensity of the background and the first and second theoretical intensities.

4. An X-ray fluorescence spectrometer for measuring intensity of secondary X-rays emitted from a sample, which includes a single layered thin film or a multi-layered thin film formed independently or on a substrate, by irradiating the sample with primary X-rays, said apparatus comprising:

a measuring line evaluating means for calculating, for each secondary X-ray line emitted from the sample, a first theoretical intensity at a specified thickness and the composition of each of the layers of the thin film and a second theoretical intensity at the thickness and the composition thereof when the thickness or the concentration has been changed by a predetermined quantity, for calculating a precision of a thickness or a precision of the concentration based on the first and second theoretical intensities, and for selecting the secondary X-ray lines to be measured based on the calculated thickness precisions or the calculated concentration precisions along with the determination of applicability or inapplicability of the analysis using the secondary X-ray lines to be measured so selected; and a display control means for causing a display unit to display the applicability or inapplicability of the analysis determined by the measuring line evaluating means.

5. The X-ray fluorescence spectrometer as claimed in claim 4, further comprising a control device for executing an analysis of the sample according to predetermined analytical conditions and wherein the measuring line evaluating means applies the selected secondary X-ray lines to be measured to the control device as a portion of the proper analytical conditions depending on the applicability or inapplicability of the analysis so determined.

6. The X-ray fluorescence spectrometer as claimed in claim 4, wherein the measuring line evaluating means calculates, for each secondary X-ray line, a theoretical intensity of a background thereof and then calculates a precision of a thickness or a precision of the concentration using the theoretical intensity of the background and the first and second theoretical intensities.

7. An X-ray fluorescence spectrometer for measuring intensities of secondary X-rays emitted from a sample, which includes a single layered thin film or a multi-layered thin film formed independently or on a substrate, by irradiating the sample with primary X-rays, said apparatus comprising:

a measuring line evaluating means for calculating, for each specified secondary X-ray line, at a thickness and a composition specified for each of the layers of the thin film, at least two numerical values from five numerical values including an overall intensity that is a theoretical intensity from the sample in its entirety; a layer intensity that is a theoretical intensity from the substrate or each layer in the thin film; a single layer intensity that is a theoretical intensity exclusive of absorption by the upper layers from the layer intensity; an attenuation ratio that is obtained by dividing the layer intensity by the single layer intensity; a ratio to infinite thickness that is a ratio of the single layer intensity at the specified thickness to the single layer intensity when the layer is deemed having infinite thickness in terms of X-rays, and to select comments from pre-stored comments for the analysis based on the calculated numerical values; and a display control means for causing a display unit to provide an indication of the numerical values and the comments both calculated and selected by the measuring line evaluating means.

* * * * *